(12) United States Patent
Polak

(10) Patent No.: US 9,113,270 B2
(45) Date of Patent: Aug. 18, 2015

(54) TRANSPOSITIONAL ACOUSTIC FREQUENCY RANGE IN EAS PATIENTS

(71) Applicant: MED-EL Elektromedizinische Geraete GmbH, Innsbruck (AT)

(72) Inventor: Marek Polak, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 378 days.

(21) Appl. No.: 13/667,142

(22) Filed: Nov. 2, 2012

(65) Prior Publication Data

US 2013/0116746 A1        May 9, 2013

Related U.S. Application Data

(60) Provisional application No. 61/555,599, filed on Nov. 4, 2011, provisional application No. 61/557,456, filed on Nov. 9, 2011.

(51) Int. Cl.
*A61N 1/36* (2006.01)
*H04R 25/00* (2006.01)
*A61F 11/04* (2006.01)
*A61N 1/05* (2006.01)

(52) U.S. Cl.
CPC .............. *H04R 25/353* (2013.01); *A61F 11/04* (2013.01); *A61N 1/0541* (2013.01); *A61N 1/36032* (2013.01)

(58) Field of Classification Search
CPC .. A61N 1/0541; A61N 1/36063; A61F 11/04; H04R 25/353

USPC ...................................................... 607/55–57
See application file for complete search history.

(56) References Cited

U.S. PATENT DOCUMENTS

2006/0287690 A1* 12/2006 Bouchataoui et al. .......... 607/57
2008/0123886 A1*  5/2008 Andersen et al. ............. 381/320
2011/0249843 A1* 10/2011 Holmberg et al. ............ 381/316

* cited by examiner

*Primary Examiner* — Tammie K Heller
(74) *Attorney, Agent, or Firm* — Sunstein Kann Murphy & Timbers LLP

(57) ABSTRACT

An electric acoustic stimulation (EAS) hearing system includes a signal processor for processing an acoustic signal input to generate: i. an electrical communications signal representative of an upper electrical range of acoustic frequencies, and ii. an acoustic communications signal representative of a lower acoustic range of acoustic frequencies, the acoustic range including: (1) a lower subrange of acoustic frequencies perceivable by the patient with amplification, and (2) an upper subrange of acoustic frequencies not perceivable by the patient, wherein the signal processor uses frequency transposition to include the upper subrange in the lower subrange. An implanted electrical stimulation subsystem receives the electrical communications signal and delivers a corresponding electrical stimulation signal to auditory neural tissue of an implanted patient. An external acoustic stimulation subsystem receives the acoustic communications signal and delivers a corresponding amplified acoustic stimulation signal to the ear canal of the patient.

4 Claims, 5 Drawing Sheets

TRANSPOSITIONAL ACOUSTIC FREQUENCY RANGE IN EAS PATIENTS

This application claims priority from U.S. Provisional Patent Application 61/555,599, filed Nov. 4, 2011, and from U.S. Provisional Patent Application 61/557,456, filed Nov. 9, 2011, which are incorporated herein by reference.

TECHNICAL FIELD

The present invention relates to hybrid electric acoustic (EAS) hearing systems.

BACKGROUND ART

A normal ear transmits sounds as shown in FIG. 1 through the outer ear 101 to the tympanic membrane 102 which moves the bones of the middle ear 103 (malleus, incus, and stapes) that vibrate the oval window and round window membrane openings of the cochlea 104. The cochlea 104 is a long narrow duct wound spirally about its axis for approximately two and a half turns in a human cochlea. It includes an upper channel known as the scala vestibuli and a lower channel known as the scala tympani, which are connected by the cochlear duct. The axial center of the cochlea 104 is called the modiolar where the spiral ganglion cells of the acoustic nerve 113 reside. In response to received sounds transmitted by the middle ear 103, the fluid-filled cochlea 104 functions as a transducer to generate electric pulses which are sensed by the acoustic nerve 113 and sent to the brain.

Hearing is impaired when there are problems in the ability to transduce external sounds into meaningful action potentials along the neural substrate of the cochlea. To improve impaired hearing, hearing prostheses have been developed. For example, when the impairment is related to operation of the middle ear, a conventional hearing aid may be used to provide acoustic-mechanical stimulation to the auditory system in the form of amplified sound to the tympanic membrane. Or when the hearing impairment is associated with the cochlea, a cochlear implant with an implanted electrode carrier can electrically stimulate adjacent auditory neural tissue with small currents.

In some patients with some residual hearing in the lower acoustic frequencies, a conventional hearing aid and a cochlear implant can be combined together in a hybrid Electric Acoustic Stimulation (EAS) system. The hearing aid acoustically amplifies lower acoustic frequencies perceived by human ear, while the cochlear implant electrically stimulates the middle and high frequencies. See von Ilberg et al, *Electric-Acoustic Stimulation of the Auditory System*, ORL 61:334-340; Skarzynski et al, *Preservation of Low Frequency Hearing in Partial Deafness Cochlear Implantation (PDCI) Using the Round Window Surgical Approach*, Acta OtoLaryngol 2007;127:41-48; Gantz & Turner, *Combining Acoustic and Electrical Speech Processing: Iowa/Nucleus Hybrid Implant*, Acta Otolaryngo12004;124:344-347; Gstöttner et al., *Hearing Preservation in Cochlear Implantation for Electric Acoustic Stimulation*, Acta Otolaryngol 2004; 124:348-352; all incorporated herein by reference.

FIG. 1 also shows some components of a typical EAS system which includes an external microphone that provides an acoustic signal input to an external signal processor 111 where two different signal processing paths are developed. An upper acoustic frequency range communications signal containing middle and high frequency range acoustic is converted into a digital data format, such as a sequence of data frames, for transmission via a transmitter coil 107 over a corresponding implanted receiver coil 106 into the electric implant 108. Besides receiving the processed acoustic information, the electric implant 108 also performs additional signal processing such as error correction, pulse formation, etc., and produces an electric stimulation pattern (based on the extracted acoustic information) that is sent through an electrode lead 109 to an implanted electrode array 110. Typically, this electrode array 110 includes multiple electrode contacts on its outer surface that provide selective electric stimulation of the cochlea 104. The external signal processor 111 also creates a lower acoustic frequency range communications signal to a conventional hearing aid 105 in the ear canal which acoustically stimulates the tympanic membrane 102, and in turn the middle ear 103 and cochlea 104.

FIG. 2 shows a graph illustrating how the acoustic frequency range is fully covered by an EAS system with the lower range of residual hearing covered by natural hearing and/or a conventional acoustic hearing aid in the ear canal while the upper acoustic frequency range where the patient shows hearing loss is covered by electrical stimulation from the cochlear implant.

SUMMARY

Embodiments of the present invention are directed to an electric acoustic stimulation (EAS) hearing system including a signal processor for processing an acoustic signal input to generate: i. an electrical communications signal representative of an upper electrical range of acoustic frequencies, and ii. an acoustic communications signal representative of a lower acoustic range of acoustic frequencies, the acoustic range including: (1) a lower subrange of acoustic frequencies perceivable by the patient with amplification, and (2) an upper subrange of acoustic frequencies not perceivable by the patient, wherein the signal processor the signal processor uses frequency transposition to include the upper subrange in the lower subrange. An implanted electrical stimulation subsystem receives the electrical communications signal and delivers a corresponding electrical stimulation signal to auditory neural tissue of an implanted patient. An external acoustic stimulation subsystem receives the acoustic communications signal and delivers a corresponding amplified acoustic stimulation signal to the ear canal of the patient.

The upper subrange may include all acoustic frequencies greater than the lower subrange and less than the electrical range. Or the upper subrange may include a lower region of acoustic frequencies greater than the lower subrange and less than the electrical range. In the latter case, the electrical range may then include acoustic information from an upper region of acoustic frequencies not perceivable by the patient and greater than the lower region, for example, using frequency transposition or frequency compression. The frequency transposition is defined as a type of processing that takes sounds in the high-frequency region and moves them to the lower frequency region.

DETAILED DESCRIPTION

Figure 1:
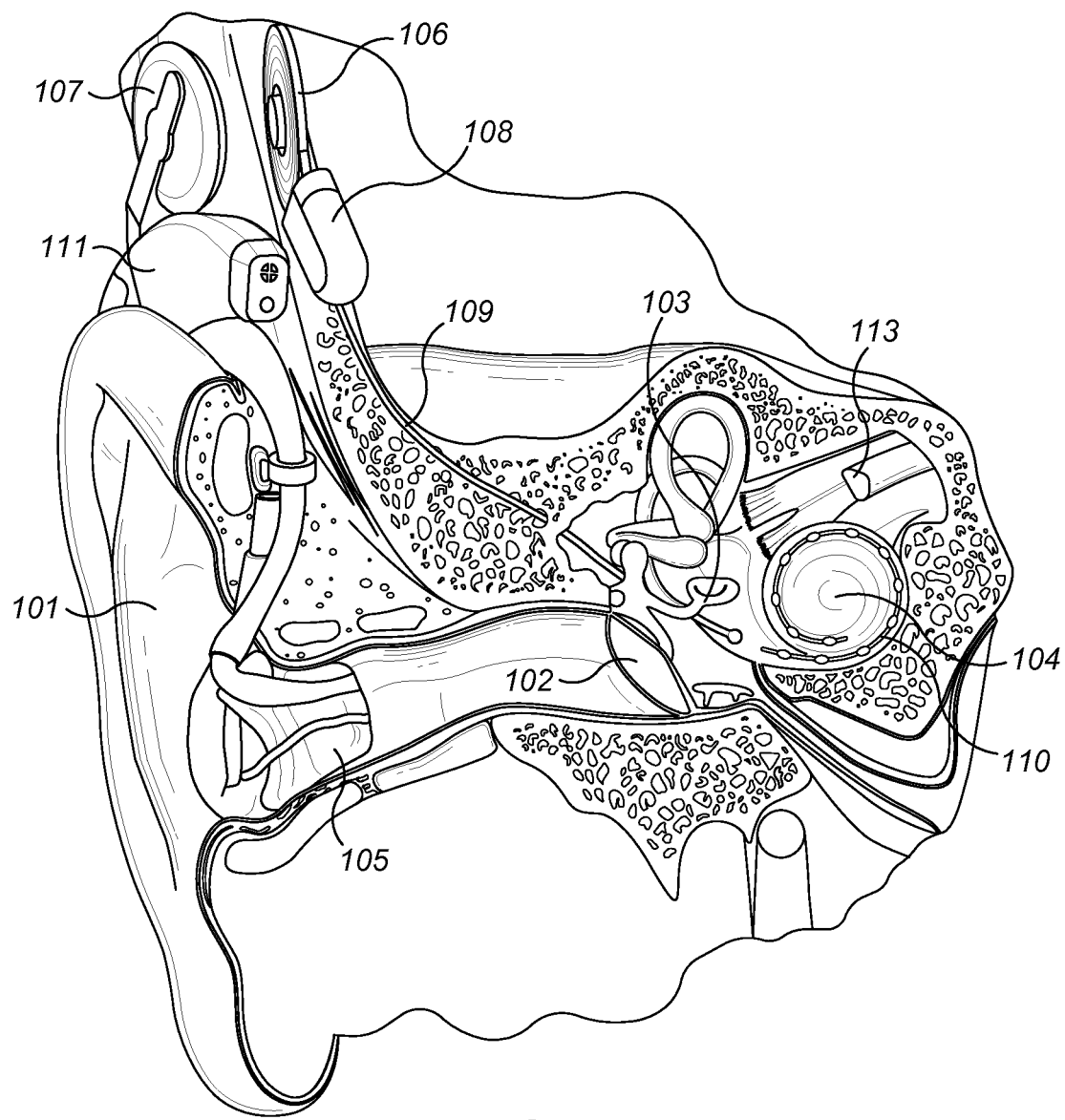
FIG. 1 shows a typical human ear having an acoustic electric hearing implant system.
Figure 2:
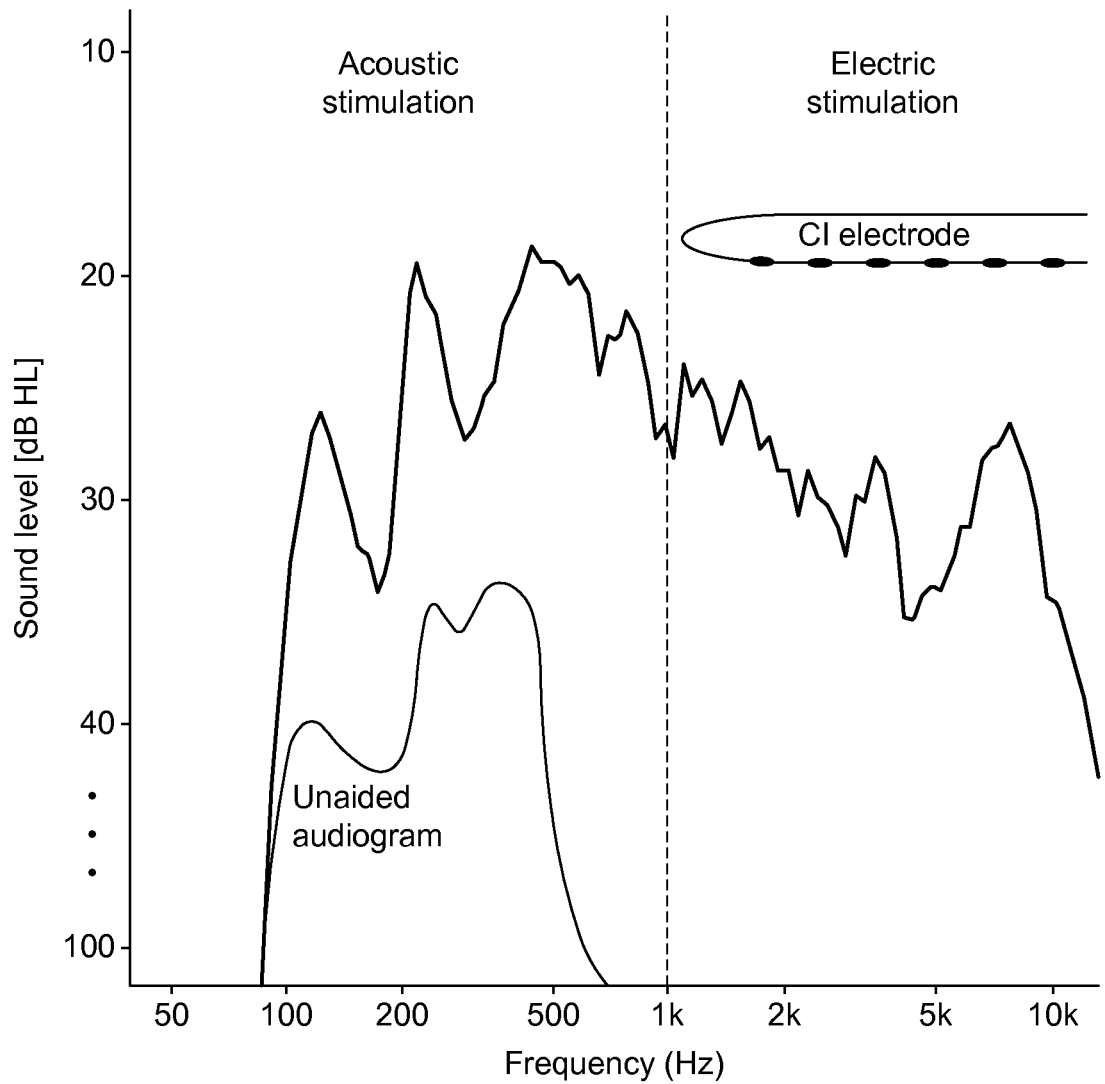
FIG. 2 shows a graph illustrating how the acoustic frequency range is fully covered by an EAS system.
Figure 3:
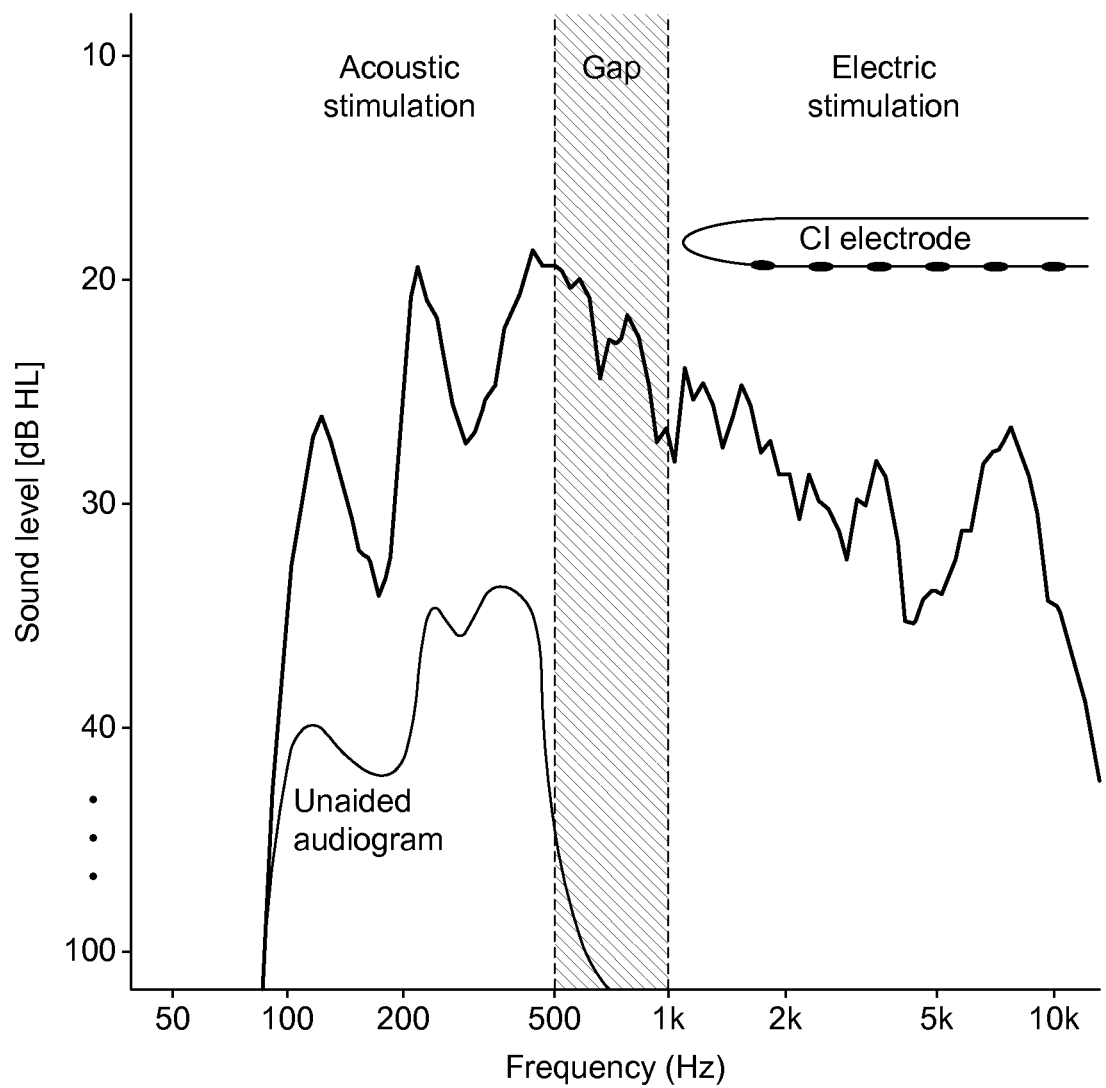
FIG. 3 shows a graph illustrating how a frequency range gap may exist with an EAS system.

In order to best preserve residual hearing, the insertion depth of an EAS electrode is controlled to a relatively shallow depth in the scala tympani which typically achieves about 360° of electrode insertion, around 18-22 mm. According to the Greenwood scale, 360° of electrode insertion in the tonotopically organized cochlea covers the acoustic frequency region from 1 kHz and higher. See Greenwood, *A Cochlear Frequency-Position Function For Several Species*—29 Years Later, J Acoustic Soc Am, 1990;87(6):2592-2605; incorporated herein by reference. Where the residual acoustic hearing frequencies are lower than 1 kHz, a frequency gap arises between the highest frequency covered by residual acoustic-based hearing and the lowest frequency covered by the electrical implant. FIG. 3 shows a graph illustrating how a frequency range gap may exist in some patients with an EAS system where the residual acoustic hearing covers acoustic frequencies up to 500 Hz and the inserted electrode hearing covers acoustic frequencies is in the range above 1 kHz. To the extent that existing EAS systems address this frequency gap at all, it is by using electrical stimulation via a cochlear implant.

Figure 4:
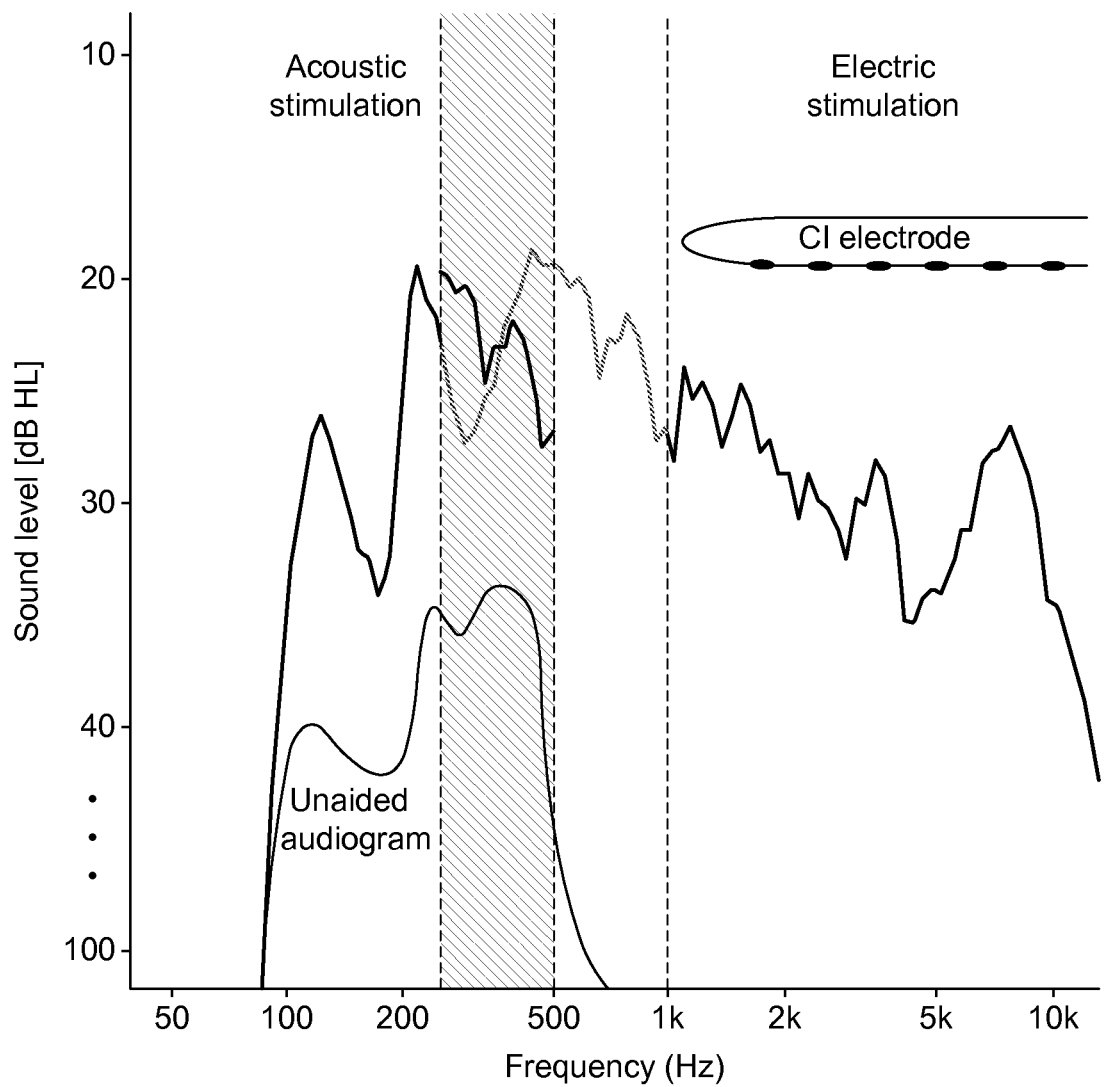
FIG. 4 shows a graph illustrating how a frequency range gap may be addressed by frequency transposition according to an embodiment of the present invention.

Embodiments of the present invention are directed to an electric acoustic stimulation (EAS) hearing system that covers such a frequency gap using transpositional acoustic amplification. FIG. 4 shows a graph illustrating how a frequency range gap may be addressed by frequency transposition, for example, by linear frequency transposition. Specifically, a signal processor (such as the external signal processor 111 or a signal processor in the electric implant 108 itself) processes an acoustic signal input to generate: i. an electrical communications signal representative of an upper electrical range of acoustic frequencies, and ii. an acoustic communications signal representative of a lower acoustic range of acoustic frequencies. And the acoustic range includes: (1) a lower subrange of acoustic frequencies perceivable by the patient with amplification, and (2) an upper subrange of acoustic frequencies not perceivable by the patient. The signal processor uses frequency transposition to include the upper subrange in the lower subrange. An implanted electrical stimulation subsystem (e.g., electrical implant 108, electrode lead 109 and electrode array 110) receives the electrical communications signal and delivers a corresponding electrical stimulation signal to auditory neural tissue of an implanted patient (e.g., in the cochlea 104). An external acoustic stimulation subsystem (e.g., hearing aid 105) receives the acoustic communications signal and delivers a corresponding amplified acoustic stimulation signal to the ear canal 102 of the patient.

The degree of the electrode insertion and the electrode insertion depth could be obtained i.e. from the postoperative CT. According to the Greenwood frequency scale, the electrical frequency coverage may be calculated. The acoustic hearing may be obtained by measuring unaided audiogram prior the fitting of the signal processor. Based on these measurements, the frequency gap for a given patient is determined In various specific embodiments, the upper subrange may include all acoustic frequencies greater than the lower subrange and less than the electrical range, or it may include a lower region of acoustic frequencies greater than the lower subrange and less than the electrical range, in which case, the electrical range may then include acoustic information from an upper region of acoustic frequencies not perceivable by the patient and greater than the lower region, for example, using frequency transposition or frequency compression.

For some patients, a frequency gap may be created intentionally and addressed by frequency transposition. For example, with deep insertion of the electrode into the cochlea (e.g., beyond 360°), one or more of the most apical electrode contacts may be turned off (not used), thereby creating a frequency gap between the usable acoustic residual hearing and the frequency range covered by the active electrode contacts. Using acoustic frequency transposition can save considerable energy in comparison to when the remaining gap is stimulated electrically. Generally an acoustic-mechanical hearing aid uses approximately 15-20% of the power consumed by current CI systems (i.e. the electrical stimulation subsystem). Thus, deactivating some certain number of apical electrodes (e.g., 3 out of 12), can dramatically decrease overall power consumption of the EAS system as a whole. Where the whole frequency gap cannot be covered by use of frequency transposition, a combination of frequency transposition for the lower frequencies and electric stimulation for the higher frequencies may be used to provide prosthetic hearing across the entire range of the frequency gap. If a patient then later loses part or all of the residual hearing, the remaining electrodes (more apical—lower frequency) that were turned off could be turned back on according to usable transpositional acoustic region and the patient should not need to significantly readjust to the change of electrical stimulation frequency range In conventional hearing aids that switch to using frequency transposition there is a significant overall increase in speech comprehension by the user. But in comparison to such conventional hearing aid applications, an EAS system generally would use deal with a much lower frequency range to transpose, and so it would be easier for EAS users to adjust. In addition, fine structure processing can be more effective by using frequency transposition than by using a regular acoustic amplification.

One of skill in the art would appreciate that the use of frequency transposition in an EAS system as described above is meaningfully different than frequency transposition as it is presently used in conventional hearing aids. While a conventional hearing aid uses the entire acoustic frequency range necessary for speech understanding, an EAS system such as described above uses a frequency gap that is specially determined based on the surgical intervention of the cochlear implant electrode (unknown before the surgery). And as compared to hypothetical use of frequency transposition in a conventional cochlear implant, the EAS system uses a residual hearing region stimulated by acoustic signals rather than electrical stimuli to dead regions of the cochlea as it is in cochlear implants. For the detailed information on dead regions see Brian C. J. Moore Dead Regions in the Cochlea: Diagnosis, Perceptual Consequences, and Implications for the Fitting of Hearing Aids. Trends In Amplification 2001; 5(1):1-34, incorporated herein by reference.

Figure 5:
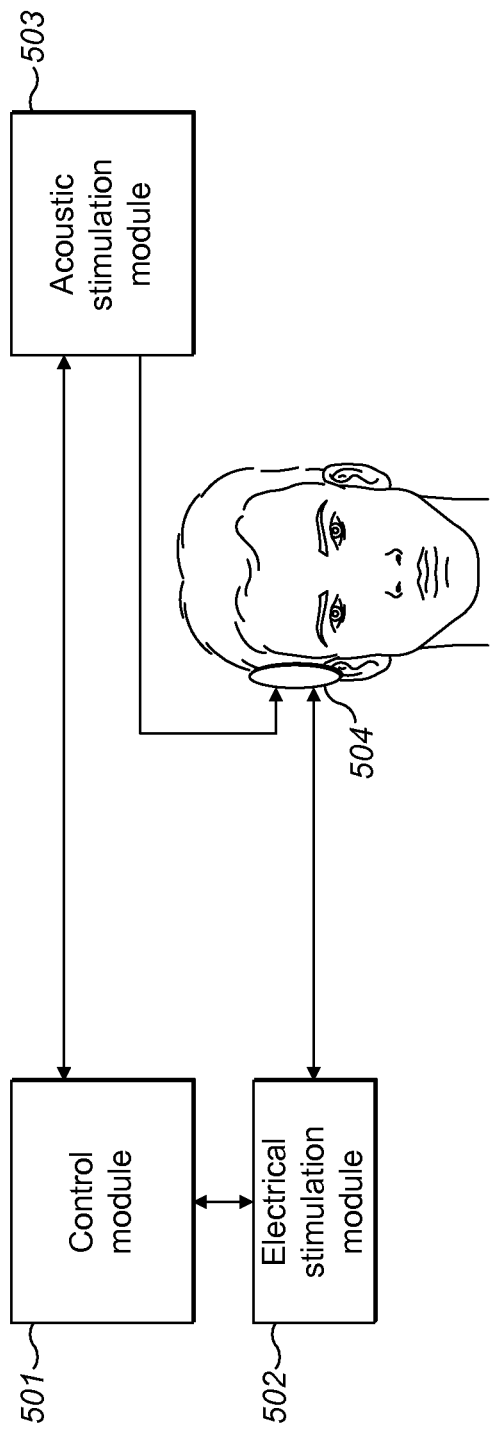
FIG. 5 shows various functional blocks in a system for patient fitting of a hybrid acoustic-electrical hearing implant system according to an embodiment of the present invention.

FIG. 5 shows various functional blocks in a system for patient fitting of a hybrid acoustic-electrical hearing implant system according to one specific embodiment of the present invention. Control module 501 contains a combination of software and hardware for controlling the stimulation of electrical and acoustical pulses. For example, control module 501 may be based on a Maestro system manufactured by Med-El, Innsbruck, Austria. The electrical stimulation pulses are transmitted from the electrical stimulation module 502 (e.g., including a Device Interface Box (DIB)) to the audio prosthesis 504 which delivers them via the cochlear implant electrodes to the target nerve tissue. The control module 501 also includes software for recording near field responses from the cochlear implant electrodes. An acoustic stimulation module 503 (e.g., including a HI-PRO Box programming interface) delivers acoustic stimuli to the audio prosthesis 504 for delivery via the ear canal to the middle ear. For example, the acoustic stimulation module 503 may be an HI-PRO Box programming interface from Noah Inc. Based on the measurements taken by the fitting system, the signal processor is being fitted and the frequency ranges of the acoustic and electric stimulation for a given patient are determined.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for an electric acoustic stimulation (EAS) hearing system comprising:
   processing an acoustic signal input to generate:
   i. an electrical communications signal representative of an upper electrical stimulation range of acoustic frequencies characterized by a lowest electrical frequency limit corresponding to a lowest acoustic frequency perceivable by ab EAS system patient via electrical stimulation, and
   ii. an acoustic communications signal representative of a lower acoustic stimulation range of acoustic frequencies, characterized by a highest acoustic frequency limit corresponding to a highest acoustic frequency perceivable by the patient via acoustic-mechanical stimulation
   wherein the highest acoustic frequency limit and/or the lowest electrical frequency limit are selected to intentionally create a frequency gap of acoustic frequencies not perceivable by the patient, and
   wherein the acoustic stimulation range contains acoustic information from the frequency gap based on frequency transposition;
   receiving the electrical communications signal with an implanted electrical stimulation subsystem that delivers a corresponding electrical stimulation signal to auditory neural tissue of the patient; and
   receiving the acoustic communications signal with an external acoustic stimulation subsystem that delivers a corresponding amplified acoustic-mechnical stimulation signal to the ear canal of the patient.

2. A method according to claim 1, wherein the acoustic stimulation range contains acoustic information from a lower range frequencies in the frequency gap, and the electrical stimulation range includes acoustic information from an upper range of frequencies in the frequency gap.

3. A method according to claim 2, wherein the acoustic information from the frequency gap is included in the electrical stimulation range by frequency transposition.

4. A method according to claim 2, wherein the acoustic information from the frequency gap is included in the electrical stimulation range by frequency compression.

* * * * *

UNITED STATES PATENT AND TRADEMARK OFFICE
CERTIFICATE OF CORRECTION

| | | |
|---|---|---|
| PATENT NO. | : 9,113,270 B2 | Page 1 of 1 |
| APPLICATION NO. | : 13/667142 | |
| DATED | : August 18, 2015 | |
| INVENTOR(S) | : Marek Polak | |

It is certified that error appears in the above-identified patent and that said Letters Patent is hereby corrected as shown below:

In The Specification

In Col. 6, line 16
replace "ab EAS"
with --an EAS--

In Col. 6, line 41
replace "range frequencies"
with --range of frequencies--

Signed and Sealed this
Ninth Day of February, 2016

Michelle K. Lee
*Director of the United States Patent and Trademark Office*